(12) United States Patent
Soni

(10) Patent No.: US 10,098,689 B2
(45) Date of Patent: Oct. 16, 2018

(54) METHODS OF MANUFACTURING JAW MEMBERS OF SURGICAL FORCEPS

(71) Applicant: COVIDIEN LP, Mansfield, MA (US)

(72) Inventor: Purvish Soni, Denver, CO (US)

(73) Assignee: COVIDIEN LP, Mansfield, MA (US)

( * ) Notice: Subject to any disclaimer, the term of this patent is extended or adjusted under 35 U.S.C. 154(b) by 226 days.

(21) Appl. No.: 15/052,451

(22) Filed: Feb. 24, 2016

(65) Prior Publication Data

US 2017/0238990 A1    Aug. 24, 2017

(51) Int. Cl.
*A61B 18/14* (2006.01)
*A61B 17/00* (2006.01)

(52) U.S. Cl.
CPC *A61B 18/1442* (2013.01); *A61B 2017/00526* (2013.01)

(58) Field of Classification Search
CPC ...... A61B 18/1445; A61B 2018/00404; A61B 2018/00601; Y10T 29/49169; Y10T 29/49174; Y10T 29/49208; Y10T 29/49181; Y10T 29/49176; Y10T 29/49128

See application file for complete search history.

(56) References Cited

U.S. PATENT DOCUMENTS

| | | | |
|---|---|---|---|
| 5,605,272 A | 2/1997 | Witt et al. | |
| 5,891,142 A | 4/1999 | Eggers et al. | |
| 5,919,206 A | 7/1999 | Gengler et al. | |
| 5,935,126 A | 8/1999 | Riza | |
| 6,077,287 A | 6/2000 | Taylor et al. | |
| 6,129,740 A | 10/2000 | Michelson | |
| 6,322,579 B1 | 11/2001 | Muller | |
| 6,334,860 B1 | 1/2002 | Dorn | |
| 6,443,968 B1 | 9/2002 | Holthaus et al. | |
| 6,506,208 B2 | 1/2003 | Hunt et al. | |
| 6,706,056 B2 | 3/2004 | Bacher | |
| 6,770,072 B1 | 8/2004 | Truckai et al. | |
| 6,790,217 B2 | 9/2004 | Schulze et al. | |
| 6,887,240 B1 | 5/2005 | Lands et al. | |
| 7,052,496 B2 | 5/2006 | Yamauchi | |
| 7,147,638 B2 | 12/2006 | Chapman et al. | |

(Continued)

OTHER PUBLICATIONS

U.S. Appl. No. 14/719,422, filed May 22, 2015, entitled "Surgical Instruments and Methods for Performing Tonsillectomy, Adenoidectomy, and Other Surgical Procedures".

*Primary Examiner* — Minh Trinh

(57) ABSTRACT

A method of manufacturing a jaw member of a surgical forceps includes forming a jaw frame having a distal jaw support. The method also includes forming an electrically-conductive defining an aperture having a first diameter, forming a stop member including a body having a second diameter smaller than the first diameter and a shoulder having a third diameter greater than the first diameter. The method also includes inserting the stop member into the aperture such that the body extends through the aperture and the shoulder abuts a portion of the electrically-conductive plate surrounding the aperture, and overmolding an outer housing about at least a portion of the jaw frame, electrically-conductive plate, and stop member to secure the jaw frame, electrically-conductive plate, and stop member to one another.

11 Claims, 5 Drawing Sheets

(56) References Cited

U.S. PATENT DOCUMENTS

| | | |
|---|---|---|
| 7,150,097 B2 * | 12/2006 | Sremcich ............ A61B 18/1445 29/854 |
| 7,384,420 B2 | 6/2008 | Dycus et al. |
| 7,494,501 B2 | 2/2009 | Ahlberg et al. |
| 7,549,988 B2 | 6/2009 | Eberl et al. |
| 7,559,940 B2 | 7/2009 | McGuire et al. |
| 7,753,909 B2 | 7/2010 | Chapman et al. |
| 7,758,608 B2 | 7/2010 | DiCesare et al. |
| 7,766,910 B2 * | 8/2010 | Hixson .............. A61B 18/1445 606/45 |
| 7,877,853 B2 | 2/2011 | Unger et al. |
| 7,922,953 B2 | 4/2011 | Guerra |
| 8,241,320 B2 | 8/2012 | Lyons et al. |
| 8,252,021 B2 | 8/2012 | Boulnois et al. |
| 8,266,783 B2 | 9/2012 | Brandt et al. |
| 8,388,646 B2 | 3/2013 | Chojin |
| 8,394,094 B2 | 3/2013 | Edwards et al. |
| 8,409,244 B2 | 4/2013 | Hinman et al. |
| 8,545,534 B2 | 10/2013 | Ahlberg et al. |
| 8,551,090 B2 | 10/2013 | Sutter et al. |
| 8,728,118 B2 | 5/2014 | Hinman et al. |
| 8,740,933 B2 | 6/2014 | Anderson |
| 8,789,741 B2 | 7/2014 | Baxter, III et al. |
| 8,814,856 B2 | 8/2014 | Elmouelhi et al. |
| 8,858,553 B2 | 10/2014 | Chojin |
| 2006/0271038 A1 | 11/2006 | Johnson et al. |
| 2009/0012520 A1 * | 1/2009 | Hixson .............. A61B 18/1445 606/51 |
| 2009/0248022 A1 | 10/2009 | Falkenstein et al. |
| 2011/0270251 A1 | 11/2011 | Horner et al. |
| 2013/0071282 A1 | 3/2013 | Fry |
| 2014/0025073 A1 | 1/2014 | Twomey et al. |
| 2017/0238990 A1 * | 8/2017 | Soni ................... A61B 18/1442 |

\* cited by examiner

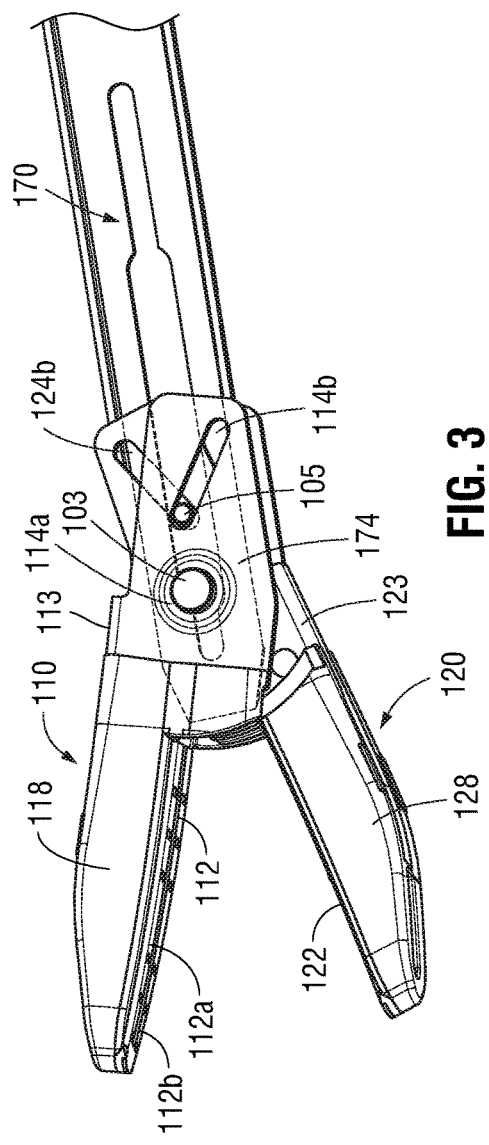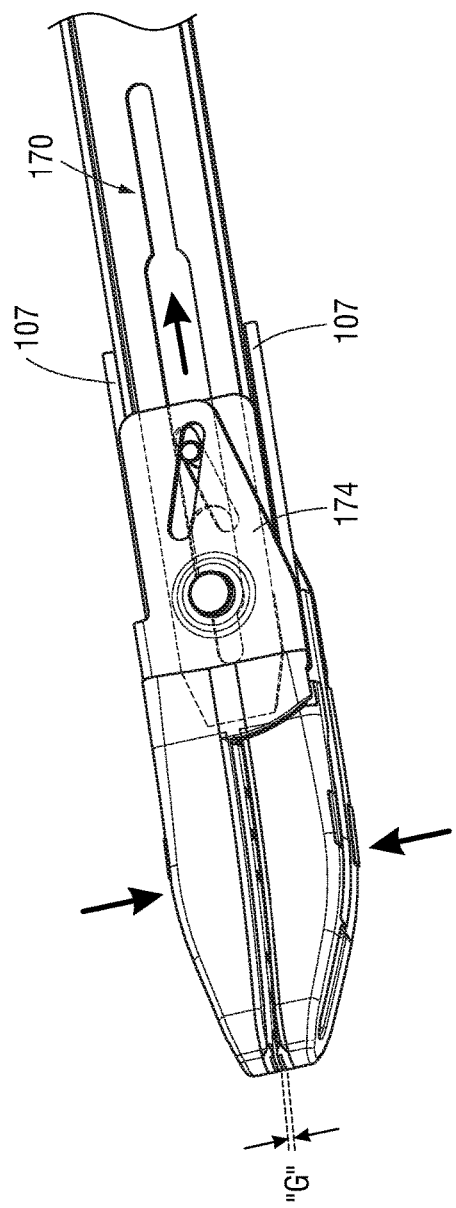

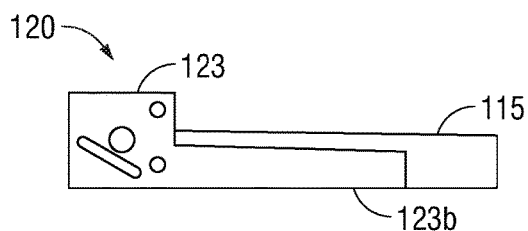 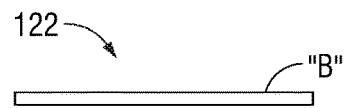
FIG. 7A  FIG. 7B
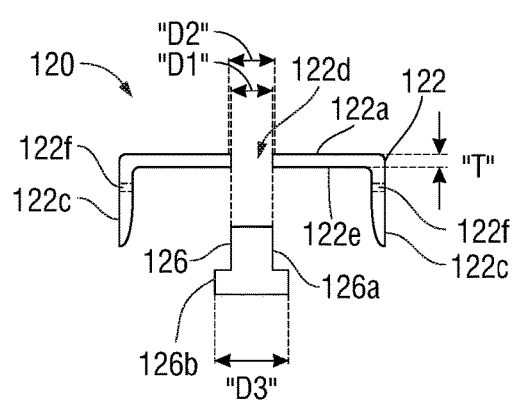 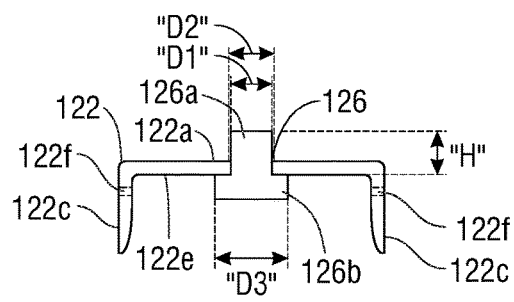
FIG. 7C  FIG. 7D
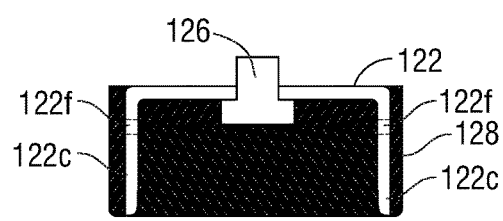
FIG. 7E

METHODS OF MANUFACTURING JAW MEMBERS OF SURGICAL FORCEPS

BACKGROUND

Technical Field

The present disclosure relates to surgical instruments and methods and, more particularly, to surgical forceps and methods for manufacturing jaw members of surgical forceps.

Background of Related Art

Open or endoscopic electrosurgical forceps utilize both mechanical clamping action and electrical energy to effect hemostasis. The electrode of each opposing jaw member is charged to a different electric potential such that when the jaw members grasp tissue, electrical energy can be selectively transferred through the tissue. A surgeon can treat tissue by either cauterizing, coagulating/desiccating, sealing, and/or simply reducing or slowing bleeding, by controlling the intensity, frequency and duration of the electrosurgical energy applied between the electrodes and through the tissue.

In order to promote accurate, consistent and effective, sealing and other tissue treatment effects, one or more insulative stop members may be positioned along one or both opposed surfaces of the jaw members to maintain a specific gap distance between the jaw members when the jaw members are in a clamping position with tissue grasped therebetween.

The stop members may be secured to the opposed surfaces of the jaw members via one or more suitable securement methods. The current techniques of forming and securing the stop members to the opposed surfaces of the jaw members may require specialty equipment, precise tolerances, and/or introduce process variability which increases the manufacturing cost of the jaw members.

SUMMARY

As used herein, the term "distal" refers to the portion that is being described which is closest to a patient, while the term "proximal" refers to the portion that is being described which is farthest from a patient. Further, to the extent consistent, any of the aspects described herein may be used in conjunction with any or all of the other aspects described herein.

A method of manufacturing a jaw member of a surgical forceps in accordance with the present disclosure includes forming a jaw frame including a distal jaw support. The method also includes forming an electrically-conductive plate defining an aperture having a first diameter, forming a stop member including a body having a second diameter smaller than the first diameter and a shoulder having a third diameter greater than the first diameter. The method also includes inserting the stop member into the aperture such that the body extends through the aperture and the shoulder abuts a portion of the electrically-conductive plate surrounding the aperture, and overmolding an outer housing about at least a portion of the jaw frame, electrically-conductive plate, and stop member to secure the jaw frame, electrically-conductive plate, and stop member to one another.

In one aspect of the present disclosure, the method further includes positioning an insulative spacer on the distal jaw support.

In another aspect the present disclosure, the electrically-conductive plate is formed via stamping.

In another aspect of the present disclosure, forming the stop member includes forming a body portion of the stop member having a height such that the body portion of the stop member extends from a tissue-contacting surface of the electrically-conductive plate a distance of between about 0.001 inches and about 0.006 inches.

In still another aspect of the present disclosure, positioning the insulative spacer on the distal jaw support includes overmolding the insulative spacer on the distal jaw support.

In yet another aspect of the present disclosure, the method further includes positioning the electrically-conductive plate and the stop member located therein on the insulative spacer and the jaw frame.

In another aspect of the present disclosure, the method further includes forming an outer housing about a portion of the jaw frame, the insulative spacer, and the electrically-conductive plate such that the jaw frame, the insulative spacer, the electrically-conductive plate, and the stop member located therein are secured in an assembled condition.

In still yet another aspect of the present disclosure, forming the electrically-conductive plate includes deforming the electrically-conductive plate to form a fill-aperture configured to locate a portion of the outer housing.

In another aspect of the present disclosure, forming the electrically-conductive plate includes deforming the electrically-conductive plate such that the electrically-conductive plate includes a thickness, wherein the difference between the height of the body portion of the stop member and the thickness of the electrically-conductive plate is between about 0.001 inches and about 0.006 inches.

In yet another aspect of the present disclosure, forming the stop member includes forming the stop member from a heat-resistant ceramic, wherein the stop member is machined from a ceramic rod or slug.

In still another aspect of the present disclosure, forming the stop member includes forming the stop member from a heat-resistant ceramic, wherein the stop member is injection molded.

According to aspects of the present disclosure, a method of manufacturing a jaw member of a surgical forceps includes stamping a blank to form an electrically-conductive plate including an aperture defining a first diameter and at least one leg defining a fill-aperture. The method also includes machining a stop member including a body having a second diameter smaller than the first diameter and a shoulder having a third diameter greater than the first diameter of the aperture. The method also includes inserting the stop member into the aperture such that the body extends through the aperture and the shoulder abuts a portion of the electrically-conductive plate surrounding the aperture, and overmolding an outer housing about a portion of the electrically-conductive plate and the stop member such that the electrically-conductive plate and the stop member are secured to one another in an assembled condition.

In an aspect of the present disclosure, the method further includes inserting the stop member into the aperture of the electrically-conductive plate such that the stop member extends from a tissue-contacting surface of the electrically-conductive plate a distance of between about 0.001 inches and about 0.006 inches.

In another aspect of the present disclosure, machining the stop member includes deforming a ceramic rod or slug.

In still another aspect of the present disclosure, the method further includes forming a jaw frame having a distal jaw support and overmolding an insulative spacer onto the distal jaw support such that the jaw frame is electrically-isolated from the electrically-conductive plate.

In yet another aspect of the present disclosure, overmolding the outer housing includes filling the fill-aperture of the electrically-conductive plate with a portion of the outer housing.

BRIEF DESCRIPTION OF THE DRAWINGS

Various aspects and features of the present disclosure described herein with reference to the drawings wherein:

FIG. 3 is a perspective view of the end effector assembly of the surgical instrument of FIG. 1 including the jaw members disposed in the spaced-apart position;

FIG. 4 is a perspective view of the end effector assembly of the surgical instrument of FIG. 1 including the jaw members disposed in the approximated position;

FIG. 7A is a longitudinal, cross-sectional view taken along section line "7A-7A" of FIG. 6 including a jaw frame and an insulative spacer disposed thereon;

FIG. 7B is a schematic view of a blank for forming an electrically-conductive plate of the jaw member of FIG. 6;

FIG. 7C is a schematic view of forming the electrically-conductive plate having an aperture and a stop member of the jaw member of FIG. 6;

FIG. 7D is a schematic view of the electrically-conductive plate having the aperture and the stop member of the jaw member of FIG. 6 disposed therein; and FIG. 7E is a schematic view of the electrically-conductive plate, the stop member, and the insulative spacer of the jaw member of FIG. 6 in an assembled condition.

DETAILED DESCRIPTION

Figure 1:
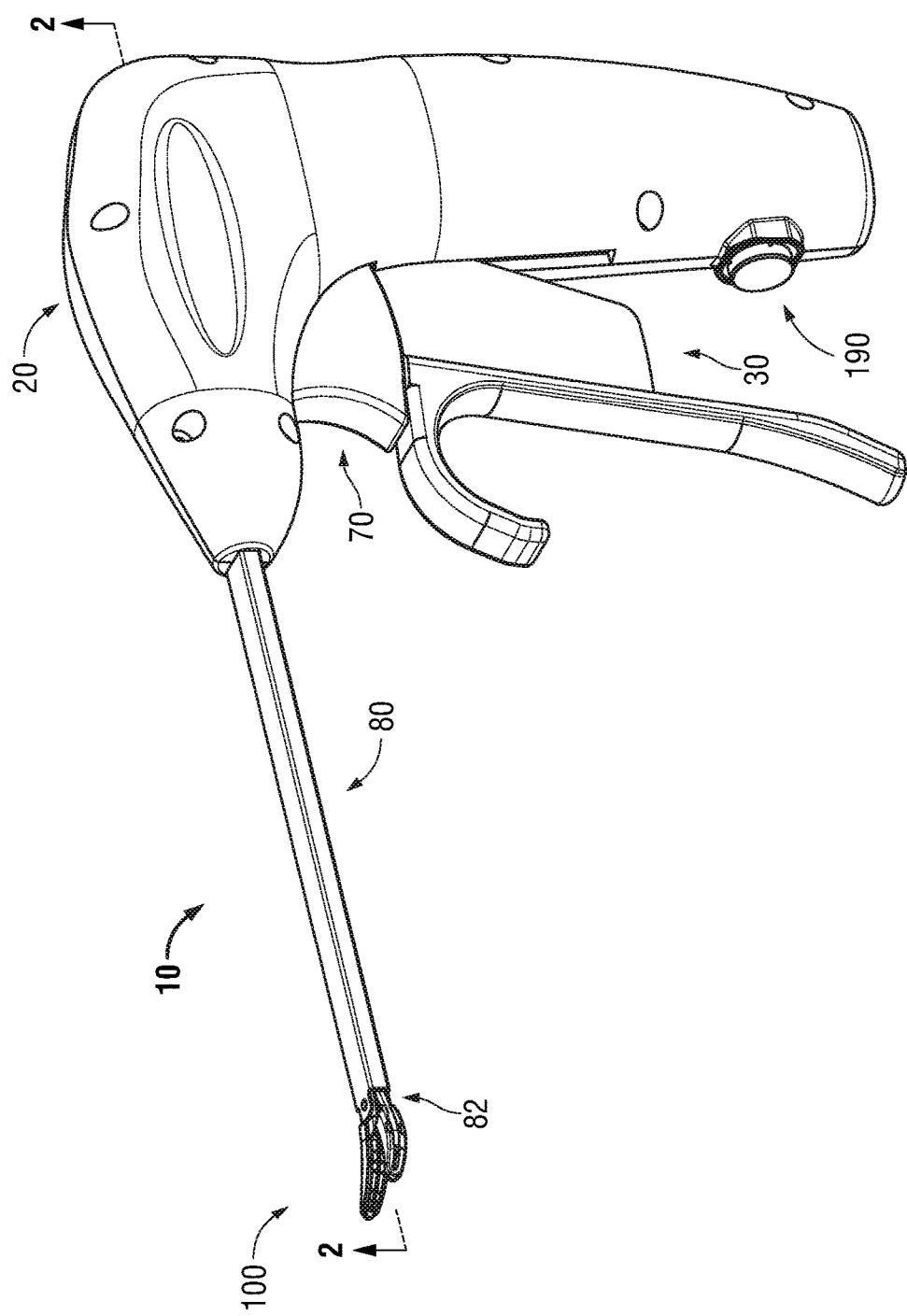
FIG. 1 is a perspective view of a surgical instrument provided in accordance with the present disclosure with jaw members of the end effector assembly of the surgical instrument disposed in a spaced-apart position.
Figure 2:
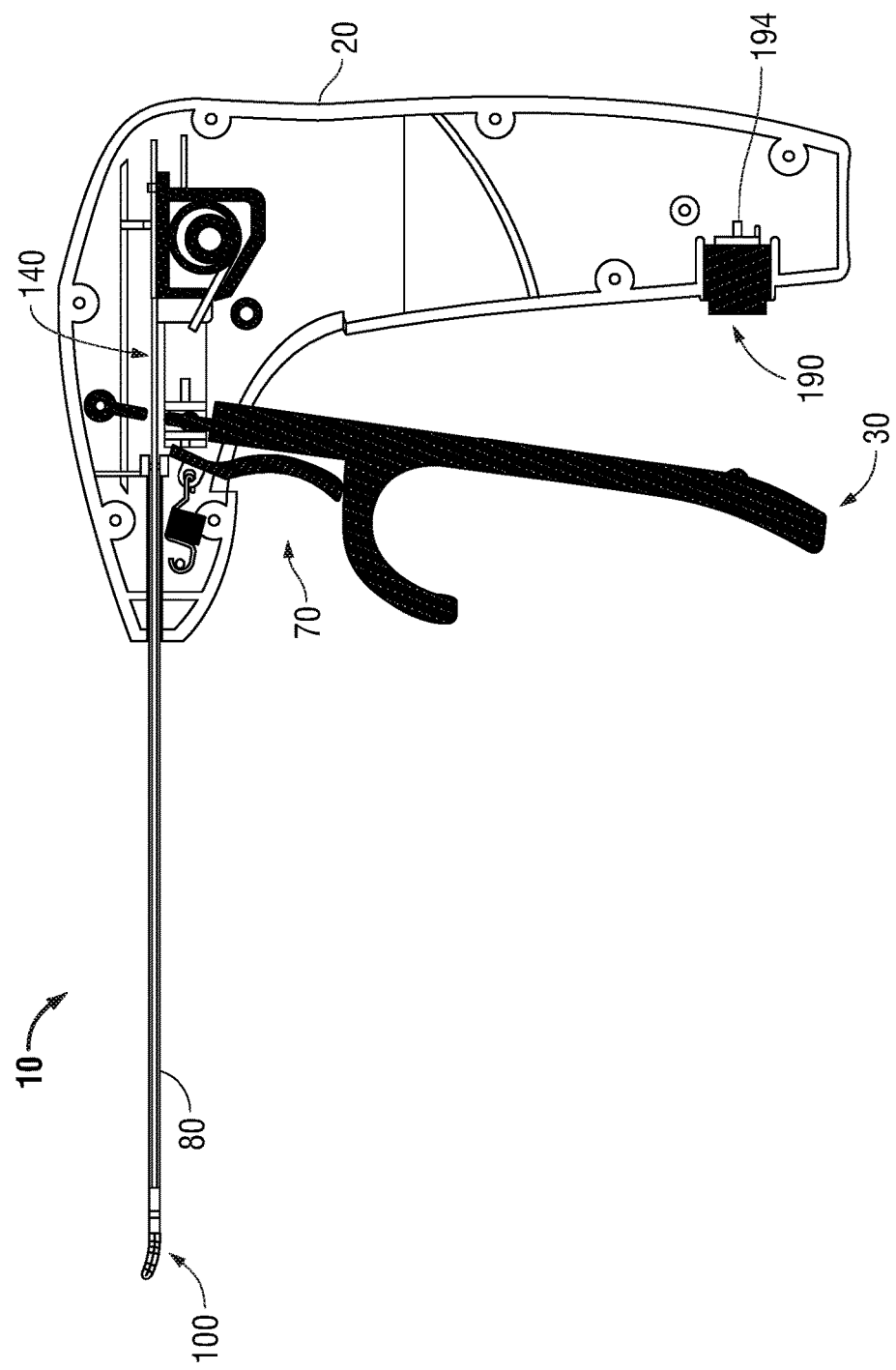
FIG. 2 is a longitudinal, cross-sectional view taken along section line "2-2" of FIG. 1.

Referring generally to FIGS. 1 and 2, a surgical instrument provided in accordance with the present disclosure is shown generally identified by reference numeral 10. Instrument 10, as described below, is configured for grasping, treating, and/or dissecting tissue and may find particular applicability for use in performing tonsillectomy and/or adenoidectomy procedures, although use of instrument 10 in various other surgical procedures is also contemplated and within the scope of the present disclosure.

With reference to FIGS. 1-4, instrument 10 generally includes a housing 20, a handle assembly 30, a trigger assembly 70, a shaft 80, an end effector assembly 100, a drive assembly 140, a knife assembly 170, and an energy activation assembly 190. Shaft 80 extends distally from housing 20 and supports end effector assembly 100 at distal end 82 thereof. Drive assembly 140 operably couples handle assembly 30 with end effector assembly 100 to enable selective manipulation of jaw members 110, 120 of end effector assembly 100. Knife assembly 170 is operably coupled with trigger assembly 70 to enable selective translation of a knife blade 174 of knife assembly 170 relative to end effector assembly 100. Energy activation assembly 190 enables energy to be selectively delivered to end effector assembly 100.

Instrument 10 may also include an electrosurgical cable (not shown) that connects instrument 10 to a generator (not shown) or other suitable power source, although instrument 10 may alternatively be configured as a battery-powered instrument. The electrosurgical cable includes lead wires, e.g., lead wires 107 (see FIG. 4), extending therethrough that have sufficient length to extend through housing 20 and shaft 80 in order to operably couple the generator, energy activation assembly 190, and end effector assembly 100 with one another to enable the selective supply of energy to electrically-conductive plates 112, 122 of jaw members 110, 120 of end effector assembly 100, e.g., upon activation of activation switch 194 of energy activation assembly 190.

For a detailed description of instrument 10, reference may be made to U.S. patent application Ser. No. 14/719,422, filed May 22, 2015, entitled "SURGICAL INSTRUMENTS AND METHODS FOR PERFORMING TONSILLECTOMY, ADENOIDECTOMY, AND OTHER SURGICAL PROCEDURES," the entire contents of which are incorporated by reference herein. However, the aspects and features of the present disclosure are equally applicable for use with other suitable surgical instruments.

Figure 5:
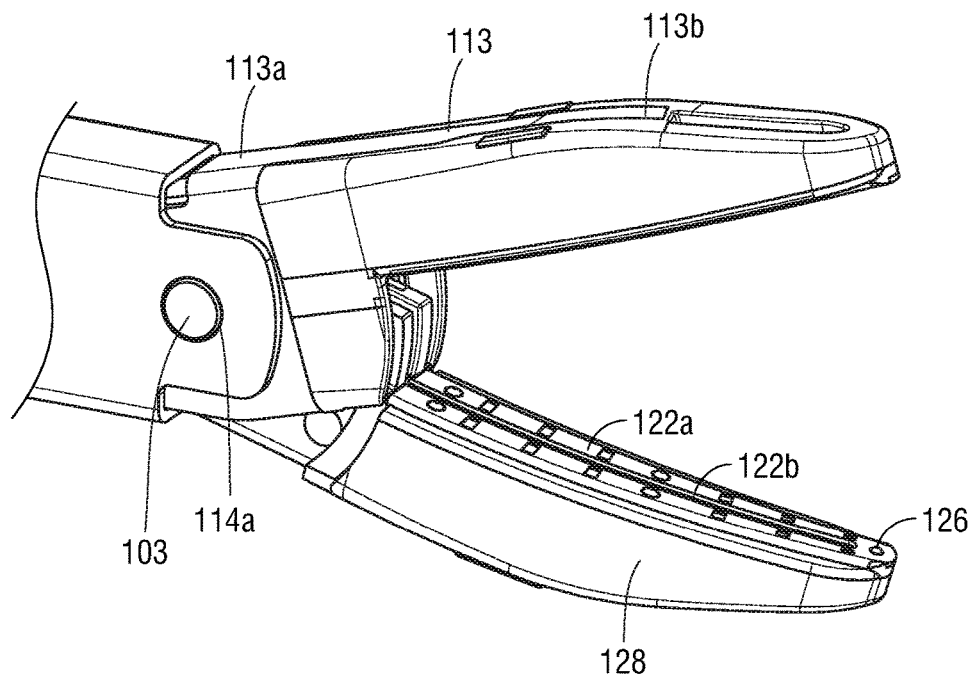
FIG. 5 is a side, perspective view of the distal end of the surgical instrument of FIG. 1 with the jaw members disposed in the spaced-apart position.
Figure 6:
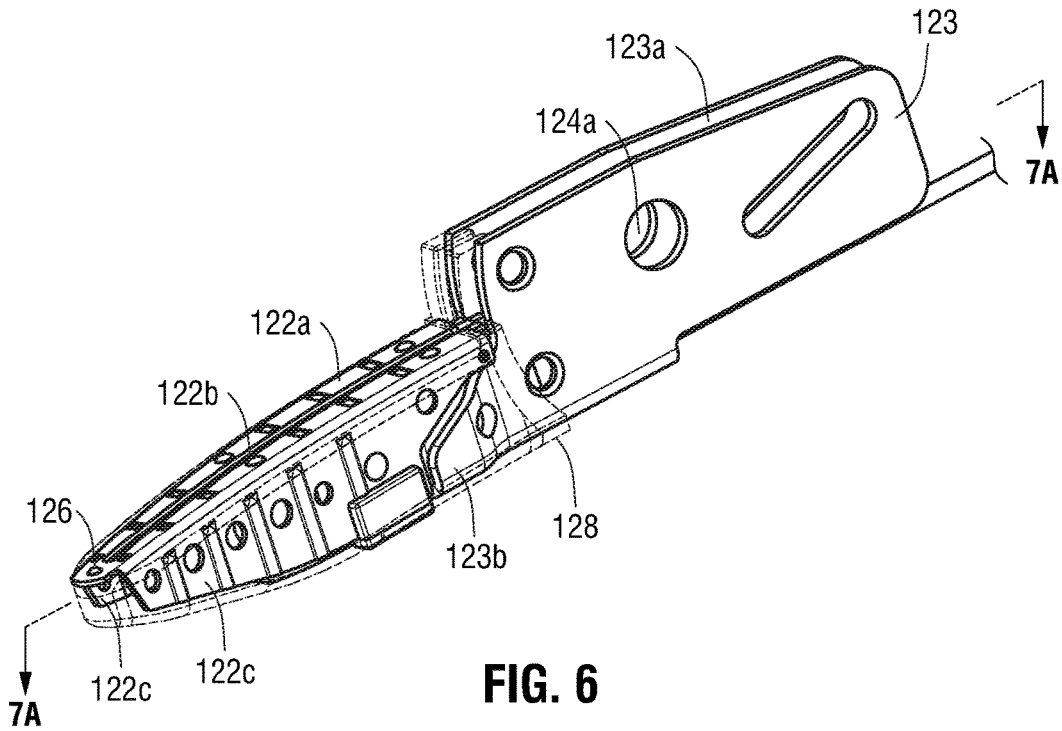
FIG. 6 is a side, perspective view of one of the jaw members of the surgical instrument of FIG. 1 with a portion thereof removed.

With additional reference to FIGS. 5 and 6, as mentioned above, end effector assembly 100 is operably supported at distal end 82 of shaft 80 and includes opposing jaw members 110, 120 pivotably coupled to one another and movable relative to one another and shaft 80 between a spaced-apart position (see FIG. 3) and an approximated position (see FIG. 4) for grasping tissue therebetween. Each jaw member 110, 120 includes an electrically-conductive plate 112, 122, a jaw frame 113, 123, an insulative spacer 115 (only insulative spacer 115 of jaw member 120 is shown, see FIGS. 7A and 7E), and an outer housing 118, 128, each of which is detailed below.

Although only the features of jaw member 110 or jaw member 120 are described below and/or illustrated in the figures, it is noted that jaw members 110, 120 defines mirror-image configurations of one another (unless specifically contradicted herein) and, thus, any description and/or illustration of one jaw member 110, 120 applies similarly to the other jaw member 110, 120.

Jaw frames 113, 123 of jaw members 110, 120 each include a pair of spaced-apart proximal flanges 113a, 123a and a distal jaw support 113b, 123b. Proximal flanges 113a of jaw member 110 are spaced-apart further than proximal flanges 123a of jaw member 120 so as to allow proximal flanges 123a of jaw member 120 to be positioned between proximal flanges 113a of jaw member 110 during assembly. Further, the proximal flanges 113a, 123a of each pair define aligned pivot apertures 114a, 124a and aligned cam slots 114b, 124b.

With brief reference to FIGS. 2 and 3, jaw members 110, 120 are pivotably coupled to one another and to shaft 80 via a pivot pin 103 such that jaw members 110, 120 are laterally movable, e.g., along the larger width dimension of shaft 80, between the spaced-apart and approximated positions. The cam slots 114b of proximal flanges 113a of jaw member 110 are oppositely angled relative to the cam slots 124b of proximal flanges 123a of jaw member 120. A camming pin 105 of end effector assembly 100 is configured for insertion through each cam slot 114b, 124b as well as a cam-pin aperture (not shown) of the drive bar (not shown) of drive assembly 140 to operably couple drive assembly 140 with jaw members 110, 120 such that translation of the drive bar of drive assembly 140 relative to jaw members 110, 120 pivots jaw members 110, 120 about pivot pin 103 and relative to one another and shaft 80 between the spaced-apart and approximated positions.

Distal jaw support 123b of jaw frame 123 of jaw member 120 extends distally from proximal flange 123a and defines a generally "L-shaped" configuration. Distal jaw support 123b is configured to support electrically-conductive plate 122, insulative spacer 115 (see FIG. 7A), and outer housing 128 of jaw member 120 thereon. However, distal jaw support 123b does not extend distally the entire length of jaw member 120. Rather, distal jaw support 123b defines a length of about 50% to about 75% of the lengths of electrically-conductive plate 122, insulative spacer 115, and outer housing 128 such that about 25% to about 50% of the lengths of these components extend distally beyond distal jaw support 123b.

The electrically-conductive plate 112, 122 of each jaw member 110, 120 defines a generally planar tissue-contacting surface 112a, 122a, an elongated slot 112b, 122b extending through the respective tissue-contacting surface 112a, 122a, and a pair of legs 122c (only legs 122c of jaw member 120 are shown) extending downwardly from each side of the respective tissue-contacting surface 112a, 122b.

Tissue-contacting surface 112a of electrically-conductive plate 112 of jaw member 110 and/or tissue-contacting surface 122a of electrically-conductive plate 122 of jaw member 120 may further include a stop member 126 operably associated therewith. For illustrative purposes, only one stop member 126 is shown in connection with jaw member 120. However, it is contemplated that jaw member 110 and/or jaw member 120 may include a plurality of stop members 126 at various different positions. Stop members 126 are configured to maintain a minimum clearance or gap distance "G" (see FIG. 4) between jaw members 110, 120 within a specified range, typically about 0.001" to about 0.006", although other ranges, depending upon a particular purpose, are also contemplated.

Outer housings 118, 128 partially enclose respective jaw members 110, 120 with the exception of a portion of the distal jaw support 113b, 123b thereof and the tissue-contacting surface 112a, 122a thereof, which remain exposed. As will be detailed below, outer housings 118, 128 are configured to secure the components of each jaw member 110, 120 in an assembled condition. Outer housings 118, 128 define lengths extending along the sides of respective jaw members 110, 120 and thicknesses that decrease in the proximal-to-distal direction along the lengths thereof.

With additional reference to FIGS. 7A-7E, the configuration and manufacture jaw members 110, 120 is detailed in accordance with the present disclosure. However, since jaw members 110, 120 define mirror-image configurations of one another, and thus include substantially similar methods of manufacture, only the configuration and manufacture of jaw member 120 is described to avoid repetition.

As noted above, jaw member 120 includes a jaw frame 123 configured to support insulative spacer 115 and electrically-conductive plate 122. Referring now to FIG. 7A, jaw frame 123 is formed via stamping and made from stainless steel, although other manufacturing processes and/or materials for forming jaw frame 123 are also contemplated. Insulative spacer 115 of jaw member 120 is formed from an electrically-insulative material and is positioned on distal jaw support 123b to electrically-isolate electrically-conductive plate 122 and distal jaw support 123b from one another. Insulative spacer 115 is overmolded onto distal jaw support 123b, although outer manufacturing processes are also contemplated.

Referring now to FIGS. 7B and 7C, electrically-conductive plate 122 of jaw member 120 is formed via stamping a blank "B" made from any suitable temperature-resistant, electrically conductive material, such as, for example, stainless steel, although other manufacturing processes and/or materials for forming electrically-conductive plate 122 are also contemplated. Blank "B" is provided and stamped to form electrically-conductive plate 122 having generally planar tissue-contacting surface 122a, elongated slot 122b (see FIG. 6), and a legs 122c, as noted above. Once formed, electrically-conductive plate 122 defines a thickness "T" between tissue-contacting surface 122a and a bottom surface 122e thereof.

During the stamping process, prior thereto, or after stamping, electrically-conductive plate 122 is punched such that an aperture 122d extends entirely through tissue-contacting surface 122a, thickness "T," and bottom surface 122e of electrically-conductive plate 122. Additionally, one or more fill-apertures 122f (see also FIG. 6) are formed on legs 122c of electrically-conductive plate 122.

Aperture 122d of electrically-conductive plate 122 is configured to locate stop member 126 therein, and as such, defines a shape corresponding to a shape of at least a portion of stop member 126. For example, in some embodiments, stop member 126 has a generally cylindrical configuration and, thus, aperture 122d has a corresponding circular shape. However, other configurations, such as, for example, square, rectangular, oval, and the like, are also contemplated.

Referring now to FIGS. 7C and 7D, stop member 126 is constructed separately from electrically-conductive plate 122. As noted above, stop member 126 is configured to create a minimum clearance or gap distance "G" between jaw members 110, 120, typically within a specified range of about 0.001" to about 0.006". Given these tight tolerances, it is contemplated that constructing stop member 126 separately from electrically-conductive plate 122, prior to inserting stop member 126 into aperture 122d of electrically-conductive plate 122, will reduce the variability in the manufacturing process, eliminate the need for precision equipment for forming stop member 126 on or with electrically-conductive plate 122, and ensure that the extension of stop member 126 through aperture 122d of electrically-conductive plate 122 will fall within the specified range of about 0.001" to about 0.006".

Stop member 126 is constructed from heat-resistant ceramic and is formed via machining ceramic rods or slugs or through an injection molding process. Alternatively, it is contemplated that stop member 126 may be constructed from other non-conductive materials, such as, for example, a high-strength thermosetting polymeric material and may be formed via other suitable manufacturing processes.

Stop member 126 is formed to include a body portion 126a and a shoulder portion 126b. Body portion 126a of stop member 126 has a diameter "D1" that is smaller than a diameter "D2" of aperture 122d of electrically-conductive plate 122 such that body portion 126a of stop member 126 may be inserted therethrough. However, in order to prevent stop member 126 from passing entirely through aperture 122d, shoulder portion 126b of stop member 126 has a diameter "D3" that is larger than diameter "D2" of aperture 122d, such that shoulder portion 126b abuts the portion of bottom surface 122e of electrically-conductive plate 122 that surrounds aperture 122d. Further, stop member 126 is formed such that body portion 126a of stop member 126 has a height "H," wherein the difference between height "H" of body portion 126a and thickness "T" of electrically-conductive plate 122 is between about 0.001" to about 0.006" so as to define a minimum gap distance "G" (FIG. 4) in that range. Alternatively, where jaw member 110 (FIGS. 3-4) includes an opposing stop member 126, the difference in height "H" of body portion 126a and thickness "T" of electrically-conductive plate 122 may be half of that noted above, such that the opposing stop members 126 cooperate to define a minimum gap distance "G" (FIG. 4) in the above-noted range. Other suitable ranges are also contemplated.

After stop member 126 is inserted into aperture 122d of electrically-conductive plate 122, the combination is positioned on insulative spacer 115, as shown in FIG. 7E. Outer housing 128 is then formed about jaw member 120 via an overmolding process, such that outer housing 128 partially encloses jaw frame 123 (FIG. 7A), electrically-conductive plate 122, and insulative spacer 115 of jaw member 120 and secures these components in position relative to one another. During the overmolding process, the plurality of fill-apertures 122f (see also FIG. 6) on legs 122c of electrically-conductive plate 122 of jaw member 120 are filled with the overmolded material forming outer housing 128 to enhance the securement of the components of jaw member 120 in an assembled condition.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of manufacturing a jaw member of a surgical forceps, comprising:
   forming a jaw frame of the jaw member, the jaw frame including a distal jaw support;
   forming an electrically-conductive plate defining an aperture having a first diameter;
   forming a stop member including a body having a second diameter smaller than the first diameter and a shoulder having a third diameter greater than the first diameter;
   inserting the stop member into the aperture such that the body extends through the aperture and the shoulder abuts a portion of the electrically-conductive plate surrounding the aperture; and
   overmolding an outer housing about at least a portion of the jaw frame, electrically-conductive plate, and stop member to secure the jaw frame, electrically-conductive plate, and stop member to one another to form the jaw member.

2. The method according to claim 1, further comprising: positioning an insulative spacer on the distal jaw support.

3. The method according to claim 2, further comprising: positioning the electrically-conductive plate and the stop member located therein on the insulative spacer and the jaw frame.

4. The method according to claim 3, further comprising: forming an outer housing about a portion of the jaw frame, the insulative spacer, and the electrically-conductive plate such that the jaw frame, the insulative spacer, the electrically-conductive plate, and the stop member located therein are secured in an assembled condition.

5. The method according to claim 4, wherein forming the electrically-conductive plate includes deforming the electrically-conductive plate to form a fill-aperture configured to locate a portion of the outer housing.

6. The method according to claim 1, wherein forming the stop member includes forming a body portion of the stop member having a height such that the body portion of the stop member extends from a tissue-contacting surface of the electrically-conductive plate a distance of between about 0.001 inches and about 0.006 inches.

7. The method according to claim 6, wherein forming the electrically-conductive plate includes deforming the electrically-conductive plate such that the electrically-conductive plate includes a thickness, wherein the difference between the height of the body portion of the stop member and the thickness of the electrically-conductive plate is between about 0.001 inches and about 0.006 inches.

8. The method according to claim 1, wherein forming the electrically-conductive plate includes forming the electrically-conductive plate via stamping.

9. The method according to claim 1, wherein positioning the insulative spacer on the distal jaw support includes overmolding the insulative spacer on the distal jaw support.

10. The method according to claim 1, wherein forming the stop member includes forming the stop member from a heat-resistant ceramic, wherein the stop member is machined from a ceramic rod or slug.

11. The method according to claim 1, wherein forming the stop member includes forming the stop member from a heat-resistant ceramic, wherein the stop member is injection molded.

\* \* \* \* \*